United States Patent
Pompa et al.

(10) Patent No.: US 8,062,595 B2
(45) Date of Patent: Nov. 22, 2011

(54) NUCLEIC ACID ANALYSIS CHIP INTEGRATING A WAVEGUIDE AND OPTICAL APPARATUS FOR THE INSPECTION OF NUCLEIC ACID PROBES

(75) Inventors: Pier Paolo Pompa, Mesagne (IT); Francesco Ferrara, Bari (IT); Ross Rinaldi, Lecce (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 365 days.

(21) Appl. No.: 12/278,265

(22) PCT Filed: Feb. 6, 2006

(86) PCT No.: PCT/IT2006/000062
§ 371 (c)(1),
(2), (4) Date: Jan. 9, 2009

(87) PCT Pub. No.: WO2007/091281
PCT Pub. Date: Aug. 16, 2007

(65) Prior Publication Data
US 2009/0312200 A1   Dec. 17, 2009

(51) Int. Cl.
*G01N 21/01* (2006.01)
(52) U.S. Cl. ....... 422/82.11; 422/69; 436/501; 436/165; 435/287.2; 73/864; 356/246; 385/12; 385/132
(58) Field of Classification Search .............. 422/82.11; 385/12, 37, 129–132; 506/39
See application file for complete search history.

(56) References Cited

U.S. PATENT DOCUMENTS

| | | | |
|---|---|---|---|
| 4,857,273 A | 8/1989 | Stewart | |
| 6,093,330 A | 7/2000 | Chong et al. | |
| 6,110,749 A * | 8/2000 | Obremski et al. | 436/527 |
| 6,192,168 B1 | 2/2001 | Feldstein et al. | |

(Continued)

FOREIGN PATENT DOCUMENTS

EP    1043770 A1    10/2000

(Continued)

OTHER PUBLICATIONS

Matthew A. Cooper: "Optical biosensors in drug discovery," Nature Reviews, Drug Discovery, Nature Publishing Group, Basingstoke, GB, vol. 1, No. 7, Jul. 2002, pp. 515-528.

(Continued)

*Primary Examiner* — In Suk Bullock
*Assistant Examiner* — Timothy G Kingan
(74) *Attorney, Agent, or Firm* — McDonnell Boehnen Hulbert & Berghoff LLP

(57) ABSTRACT

A chip for nucleic acid analysis includes a body (2, 9), in which a detection chamber (7) is formed for accommodating nucleic acid probes (12, 12'). A waveguide (8) is integrated in the body (2, 9) is and is arranged at the bottom of the detection chamber (7) so that an evanescent wave (EW), produced at an interface (8a) of the waveguide (8) when a light radiation is conveyed within the waveguide (8), is irradiated towards the inside of the detection chamber (7). An apparatus for inspection of nucleic acid probes includes: a holder (22), on which a chip (1) for nucleic acid analysis is loaded, the chip containing nucleic acid probes (12, 12'); a light source (24) for supplying an excitation radiation to the nucleic acid probes (12, 12'); and an optical sensor (25) arranged so as to receive radiation coming from the nucleic acid probes (12, 12').

16 Claims, 5 Drawing Sheets

U.S. PATENT DOCUMENTS

| | | | |
|---|---|---|---|
| 2002/0147317 A1* | 10/2002 | Bentsen et al. | 536/8 |
| 2003/0228583 A1* | 12/2003 | Amacher et al. | 435/6 |
| 2004/0206749 A1 | 10/2004 | Villa et al. | |
| 2005/0141833 A1* | 6/2005 | Barros et al. | 385/123 |
| 2005/0202504 A1* | 9/2005 | Anderson et al. | 435/6 |
| 2005/0282221 A1 | 12/2005 | Barlocchi et al. | |

FOREIGN PATENT DOCUMENTS

| | | |
|---|---|---|
| EP | 1130631 A1 | 9/2001 |
| EP | 1 400 600 A | 3/2004 |

OTHER PUBLICATIONS

Cheryl L. Baird et al.: "Current and emerging commercial optical biosensors," Journal of Molecular Recognition : JMR, Sep. 2001, vol. 14, No. 5, pp. 261-268.

Don I Stimpson et al.: "Real-time detection of DNA hybridization and melting on oligonucleotide arrays by using optical wave guides," Proceedings of the National Academy of Sciences of USA, National Academy of Science, Washington, DC, US, vol. 92, Jul. 1995, pp. 6379-6383.

Jesus M. Ruano et al.: "Flame Hydrolysis Deposition of Glass on Silicon for the Integration of Optical and Microfluidic Devices," Analytical Chemistry, American Chemical Society, Columbus, US, vol. 72, No. 5, Mar. 1, 2000, pp. 1093-1097.

Athanasios N. Chryssis et al.: "Detecting hybridization of DNA by highly sensitive evanescent field etched core fiber Bragg grating sensors," IEEE Journal of Selected Topics in Quantum Electronics IEEE USA, vol. 11, No. 4, Jul. 2005, pp. 864-872.

T.E. Plowman et al., "Multiple-Analyte Fluoroimmunoassay Using an Integrated Optical Waveguide Sensor," Analytical Chemistry, vol. 71, pp. 4344-4352 (1999).

S. Rodriguez-Mozaz et al., "Simultaneous multi-analyte determination of estrone, isoproturon and atrazine in natural waters by the River ANAlyser (RIANA), an optical immunosensor," Biosensors and Bioelectronics, vol. 19, pp. 633-640 (2004).

Office Action, dated Mar. 23, 2010, from related Chinese Patent Application No. 200680054068.

* cited by examiner

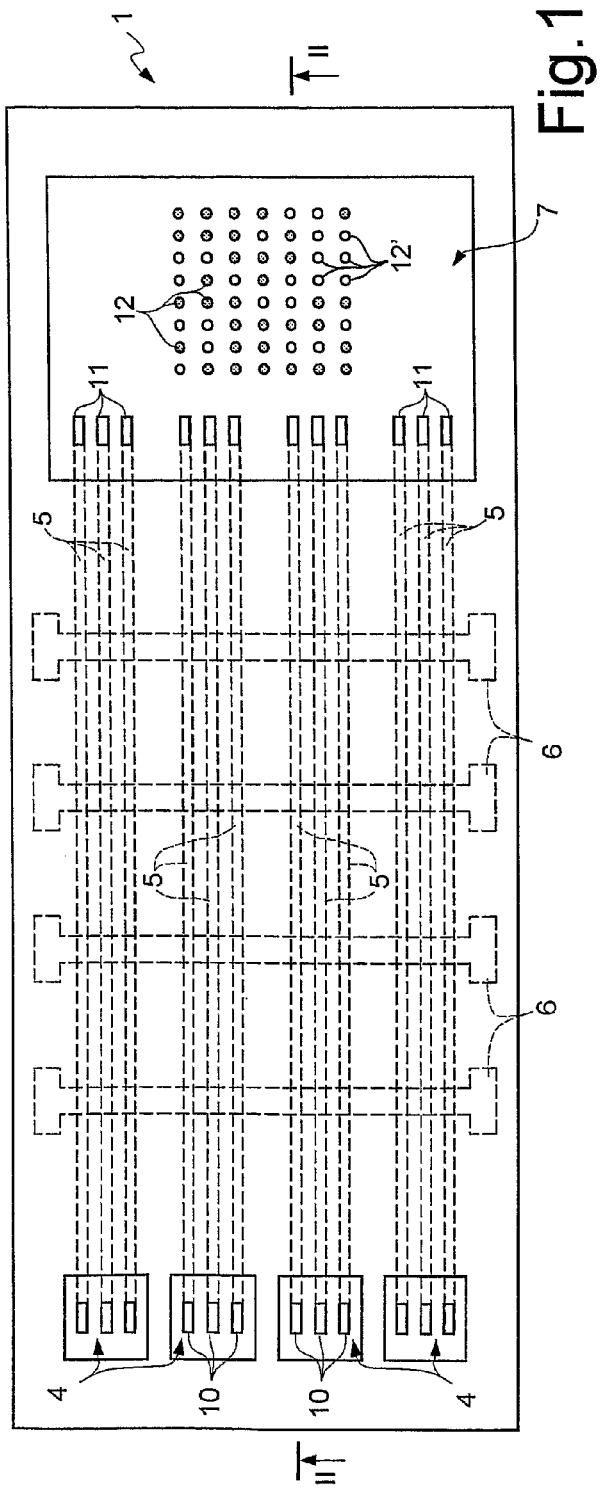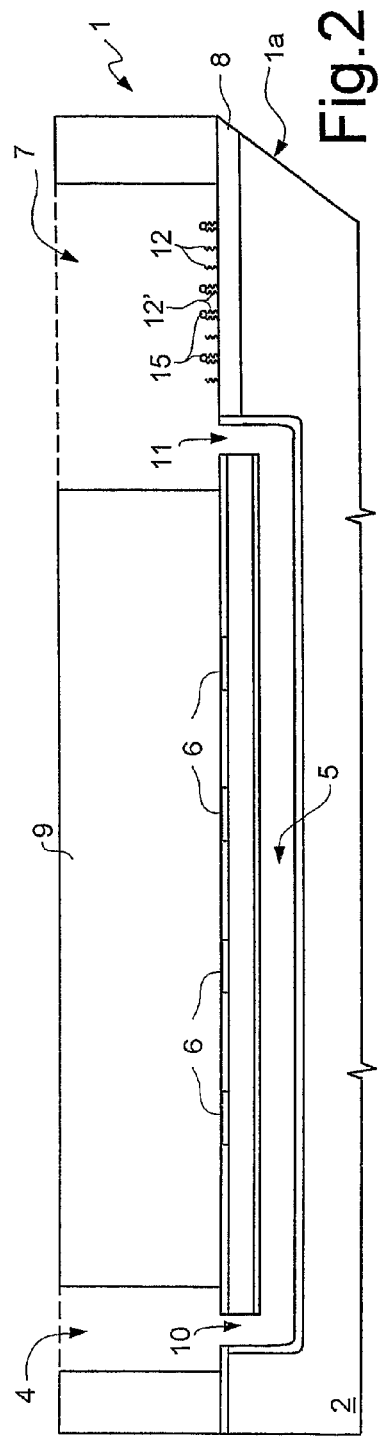

NUCLEIC ACID ANALYSIS CHIP INTEGRATING A WAVEGUIDE AND OPTICAL APPARATUS FOR THE INSPECTION OF NUCLEIC ACID PROBES

TECHNICAL FIELD

The present invention relates to a chip for nucleic acid analysis, which integrates a waveguide, and to an optical apparatus for inspection of nucleic acid probes.

BACKGROUND ART

As is known, the analysis of nucleic acids requires, according to different modalities, preliminary steps of preparation of a sample of biological material, of amplification of the nucleic material contained therein, and of hybridization of individual target or reference strands, corresponding to the sequences sought. Hybridization occurs (and the test yields a positive outcome) if the sample contains strands complementary to the target strands.

At the end of the preparatory steps, the sample must be examined to control whether hybridization has occurred (the so called detection step). For this purpose, various inspection methods and apparatuses are known, for example of an optical or electrical type. In particular, the methods and apparatuses of an optical type are frequently based upon the phenomenon of fluorescence. The reactions of amplification and hybridization are conducted so that the hybridized strands, contained in a detection chamber made in a support, include fluorescent molecules or fluorofors (the hybridized strands may be either grafted to the bottom of the detection chamber or remain in liquid suspension). The support is exposed to a light source having an appropriate spectrum of emission, such as to excite the fluorofors. In turn, the excited fluorofors emit a secondary radiation at an emission wavelength higher than the peak of the excitation spectrum. The light emitted by the fluorofors is collected and captured by an optical sensor. In order to eliminate the background light radiation, which represents a source of disturbance, the optical sensor is provided with band-pass or interferential filters centred at the wavelength of emission of the fluorofors.

However, the difference between the maximum peak of the emission spectrum of the fluorofors and the peak of the excitation spectrum (also referred to as "Stokes shift") is not very high, and the filters, however selective they may be, can only attenuate the light emitted by the source and subsequently diffused, without, however, eliminating it altogether. It should also be taken into account that the materials used for providing the supports often have high reflecting power. For example, microfluidic devices for the analysis of nucleic acids integrated in semiconductor chips are increasingly widespread. In integrated microfluidic devices, the detection chamber often has the bottom coated with a layer of silicon dioxide and, sometimes, also metal electrodes are present, for example of gold or aluminium. In effect, hence, only a relatively small part of the light emitted by the source is absorbed, whereas a conspicuous fraction is reflected and is potentially capable of disturbing the detection of the light emitted by the fluorofors.

DISCLOSURE OF INVENTION

The aim of the present invention is to provide a chip for analysis of nucleic acids and an optical apparatus for the inspection of nucleic acid probes that will enable the limitations described to be overcome.

According to the present invention, a chip for analysis of nucleic acids and an optical apparatus for the inspection of nucleic acid probes are provided, as defined in claims 1 and 13, respectively.

BRIEF DESCRIPTION OF THE DRAWINGS

For a better understanding of the invention, an embodiment thereof is now described, purely by way of non-limiting example and with reference to the attached plate of drawings, wherein:

FIG. 1 is a top plan view of a chip for analysis of nucleic acids in accordance with a first embodiment of the present invention;

FIG. 2 is a cross-sectional view through the chip of FIG. 1, taken according to the line II-II of FIG. 1;

BEST MODE FOR CARRYING OUT THE INVENTION

Figure 3:
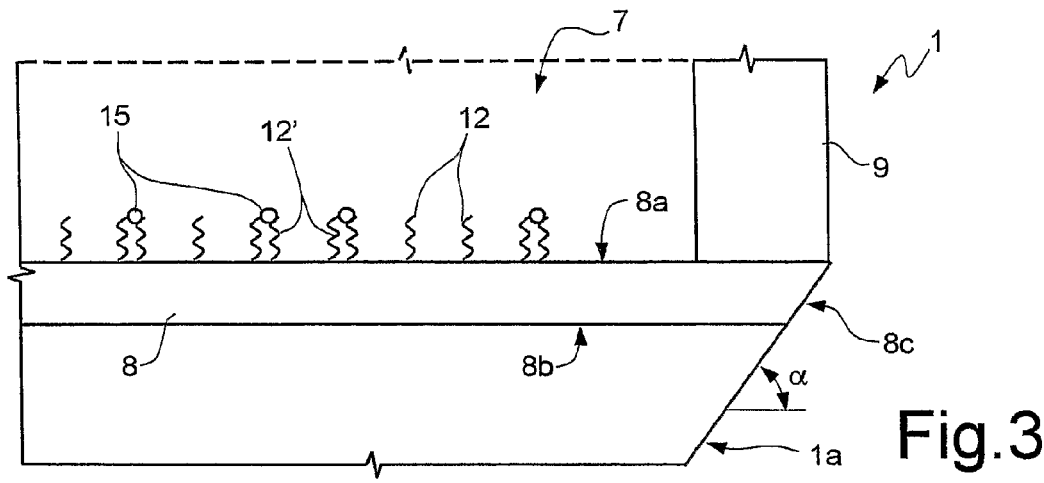
FIG. 3 shows an enlarged detail of the view of FIG. 2.

FIGS. 1 and 2 show a chip 1 in which a chemical microreactor for the analysis of nucleic acids (here DNA) is provided. The chip 1 comprises: a substrate 2 made of semiconductor material; inlet reservoirs 4; a plurality of microfluidic channels 5; heaters 6 associated to the microfluidic channels 5; a detection chamber 7; and a waveguide 8.

More precisely, the inlet reservoirs 4 and the detection chamber 7 are defined in a structural layer 9 arranged on the surface of the substrate 2 (for example, the structural layer 9 may either comprise a resist layer deposited on the substrate 2 or a glass chip glued thereto).

The microfluidic channels 5 are buried within the substrate 2, for example as described in EP-A-1 043 770, in EP-A-1 130 631 or in the published patent application US 2005/282221, and extend between the inlet reservoirs 4 and the detection chamber 7. Furthermore, the microfluidic channels 5 are fluidly coupled both to the inlet reservoirs 4, through inlet openings 10, so as to be accessible from outside, and to the detection chamber 7, through outlet openings 11.

The heaters 6, here including resistive elements made of polysilicon, are formed on the surface of the substrate 2 and extend in a direction transverse to the microfluidic channels 5. Furthermore, the heaters 6 are electrically connectable in a known way to external electric power sources (not shown) and can be driven to release thermal power to the microfluidic channels 5 so as to cyclically control the temperature within them according to predetermined thermal profiles.

The detection chamber 7 is designed to receive a fluid containing previously processed nucleic material in suspension, to perform a step of optical detection of nucleic acid sequences. As illustrated in greater detail in FIG. 3, the detection chamber 7 is formed above the waveguide 8 and accommodates a plurality of so-called "DNA probes" 12, comprising single-stranded reference DNA containing predetermined sequences of nucleotides. More precisely, the DNA probes 12 are arranged in predetermined positions so as to form an array and are grafted directly to the waveguide 8, which forms the bottom of the detection chamber 7. After a step of hybridization, some of the DNA probes, designated by 12', are hybridized, i.e., they are bound to individual complementary DNA sequences, and contain fluorofors 15.

The waveguide 8 is formed on the substrate 2 and extends at least under the array of DNA probes 12, 12' and, preferably, at the bottom of the entire detection chamber 7. Furthermore, the waveguide 8 comprises a plane layer of optically conductive material having a predetermined primary refraction index $N_1$. For example, silicon oxynitride or silicon dioxide may be used, appropriately doped with germanium, phosphorus or boron (the value of the primary refraction index $N_1$ depends in fact upon the concentration of the dopant species). Alternatively, it is possible to diffuse titanium, obtaining a guiding effect by ion exchange.

The waveguide 8 is defined on one side by a first interface 8a, with the inside of the detection chamber 7, and on an opposite side by a second interface 8b, with the substrate 2. The primary refraction index $N_1$ is chosen so that the energy associated to electromagnetic radiation conveyed in the waveguide 8 will in part remain confined inside it, with the exception of a predetermined fraction or tail, which leaves the waveguide (evanescent wave). More precisely (see also FIG. 8), the primary refraction index $N_1$ is selected in relation to a secondary refraction index $N_2$, which is characteristic of the fluid introduced into the detection chamber 7 for the detection step, so that the electromagnetic energy exiting through the first interface 8a (energy of the evanescent wave EW) is a predetermined fraction of the total. Furthermore, the relation between the primary refraction index $N_1$ and the secondary refraction index $N_2$ is such that the intensity of the evanescent wave EW becomes substantially negligible at an attenuation distance $D_0$ of approximately 1-2 μm from the first interface 8a.

Preferably, the ratio between the primary refraction index $N_1$ of the waveguide 8 and a refraction index of the substrate 2 is such as to prevent substantially the dispersion of energy through the second interface 8b.

As illustrated in the detail of FIG. 3, a face 1a of the chip 1, designed to be exposed to a light source of external excitation, is cut so as to form a predetermined angle with respect to the first interface 8a and the second interface 8b. An outer edge of the waveguide 8 is exposed on the face 1a and defines an optical coupling surface 8c for conveying visible electromagnetic radiation from outside in the direction of the waveguide 8.

Figure 4:
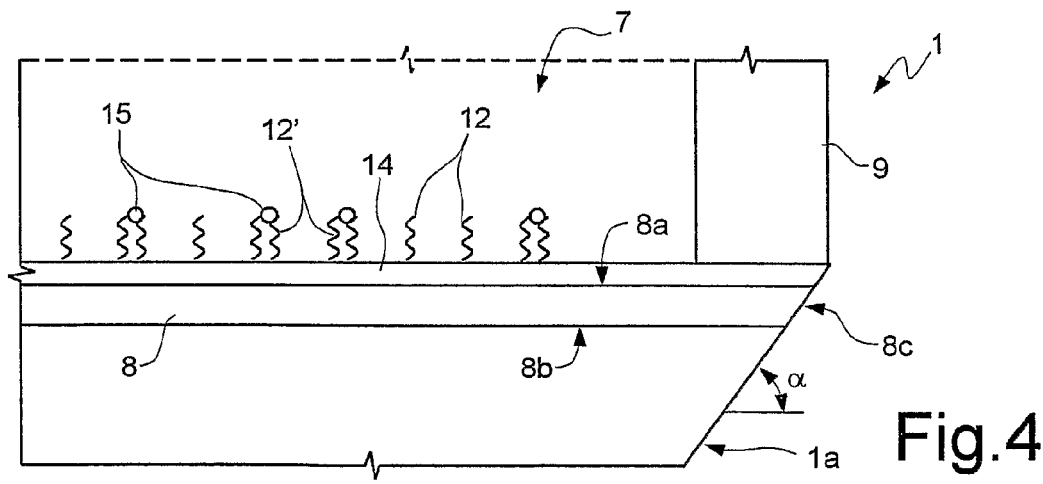
FIGS. 4 and 5 show a first variant and a second variant of the chip of FIG. 1.

In the variant illustrated in FIG. 4, the DNA probes 12 are grafted to an anchorage layer 14 deposited on the waveguide 8. In this case, the first interface 8a is defined between the waveguide 8 and the anchorage layer 14. The primary refraction index $N_1$ is determined taking into account also the refraction index and the thickness of the anchorage layer 14. In practice, the attenuation distance of the evanescent wave (from the first interface 8a) is approximately 1-2 μm greater than the thickness of the anchorage layer 14.

Figure 5:
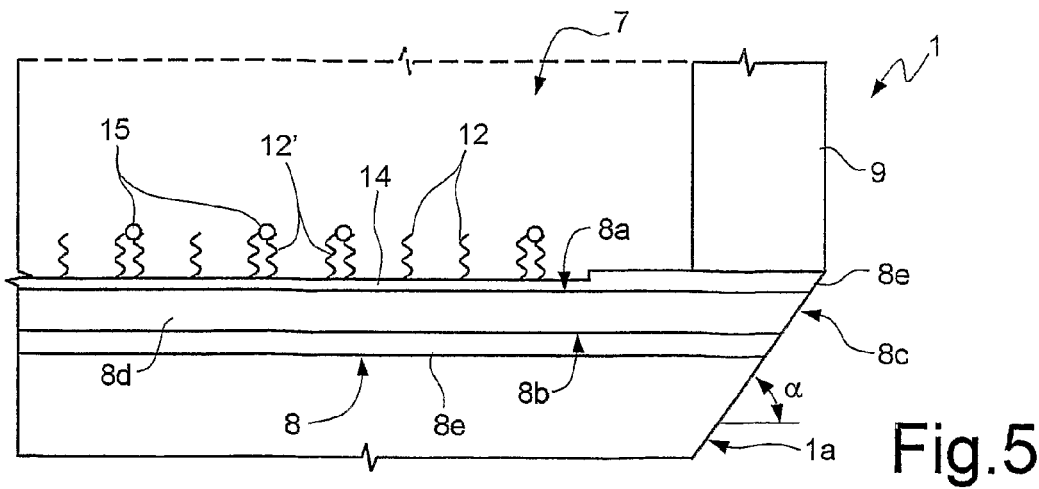

In the further variant illustrated in FIG. 5, the light guide 8 comprises a core 8d, having the primary refraction index $N_1$, and a cladding 8e, which coats both of the faces of the core 8d and has a secondary refraction index $N_2$. In this case, the first interface 8a is defined between the core 8d and the cladding 8e, on the side to which the DNA probes 12 are anchored. Preferably, the cladding 8e is thinned out where the DNA probes 12 are anchored, to favour excitation of the fluorofors 15 that may possibly present. If need be, an anchorage layer for the DNA probes 12 (here not shown) can be envisaged.

The microreactor integrated in the chip 1 is prearranged for performing reactions of amplification of nucleic material, for example by PCR (Polymerase Chain Reaction) and hybridization of the DNA probes 12. For this purpose, a biological sample in liquid suspension, containing nucleic material previously treated, is supplied to the inlet reservoirs 4 and fed into the microfluidic channels 5. Here, the sample is subjected to thermal cycling in order to amplify the DNA present in a known way. At the end of the amplification step, the biological sample is further made to advance as far as the detection chamber 7, where the DNA probes 12 are located. If the biological sample contains sequences of nucleotides complementary to the DNA probes 12, the latter are hybridized. Furthermore, the amplification reactions are conducted so that the hybridized DNA probes 12' will contain fluorofors 15 (shown only schematically) having a characteristic emission wavelength.

Figure 6:
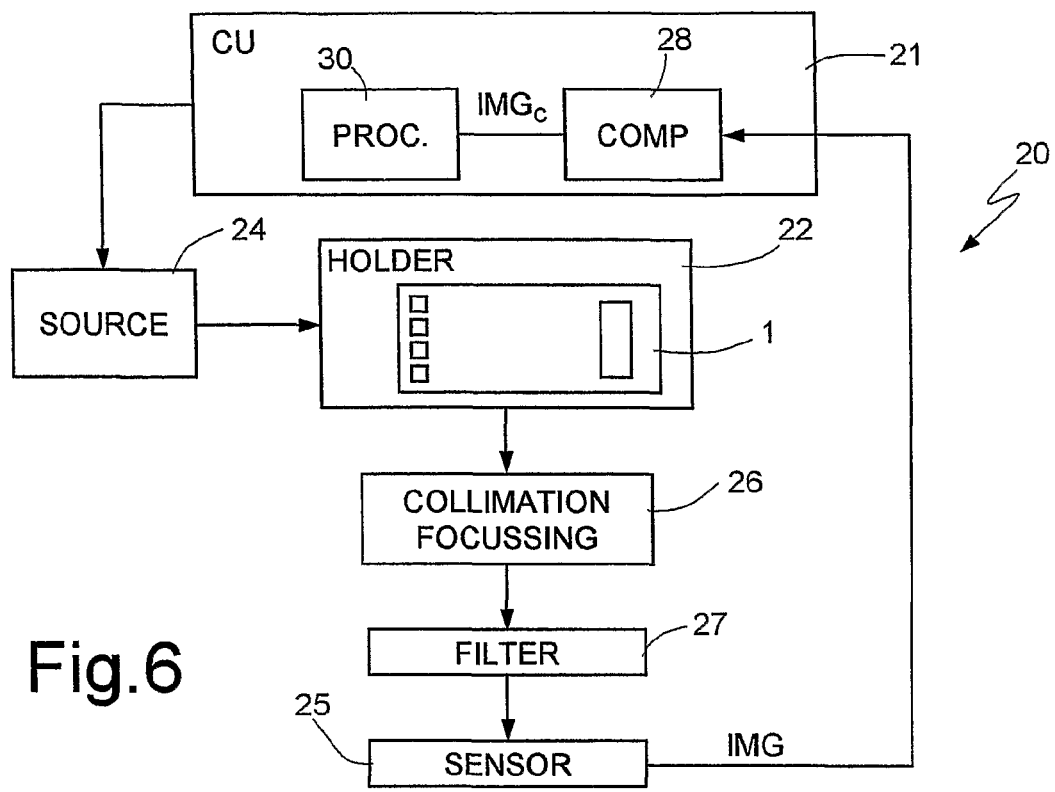
FIG. 6 is a simplified block diagram of an optical inspection apparatus for the detection of nucleic acids, which uses the chip of FIG. 1.
Figure 7:
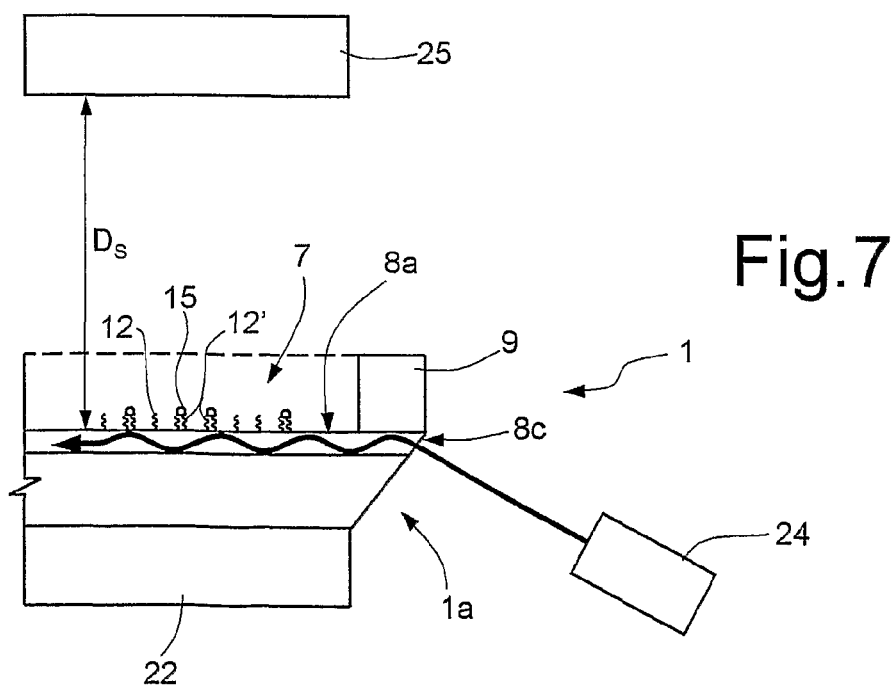
FIG. 7 is a schematic illustration of a detail of the chip of FIG. 1 loaded into the apparatus of FIG. 6.

With reference to FIGS. 6 and 7, the number 20 designates an optical inspection apparatus for the detection of hybridized DNA strands, based upon fluorescence. The inspection apparatus 20 comprises a control unit 21, a holder 22 for housing an item of the chip 1, a light source 24 and an optical sensor 25, provided with a collimation and focusing device 26, and a filter 27, having passband centred around the wavelength of emission characteristic of the fluorofors 15.

Furthermore, the control unit 21 comprises a compensator module 28, which receives digital images IMG from the optical sensor 25, and an image processing module 30.

FIG. 7 shows a detail of the chip 1 loaded into the holder 22 so as to be examined. The light source 24 emits electromagnetic radiation with a spectrum such as to excite the fluorofors 15 and may comprise a laser (coherent monochromatic source) or else a conventional incandescent lamp or a LED, with appropriate optical filters (incoherent source). When the chip 1 with the integrated microreactor is located in the holder 22 in a reading position, the light source 24 is optically coupled to the waveguide 8. More precisely, the light source 24 is arranged so that the light emitted is directed towards the face 1a of the chip 1. Furthermore, the orientation of the light source 24 is such that the radiation incident on the optical coupling surface 8c of the waveguide 8 is conveyed along the waveguide 8 itself.

The optical sensor 25, for example of a CMOS or CCD type, is arranged so as to collect the light emitted by the fluorofors 15 present in the detection chamber 7 of the microreactor integrated in the chip 1. In practice, when the chip 1 is loaded into the holder 22, the optical sensor 25 is substantially parallel to the first interface 8a, at a detection distance $D_S$ much greater than the attenuation distance $D_0$, for example approximately 3-7 cm.

The inspection apparatus 20 operates in the way described hereinafter. Initially, an item of the chip 1, integrating a microreactor in which a step of hybridization of the DNA probes 12 has been carried out, is loaded into the holder 22. The control unit 21 activates the light source 24, and part of the excitation radiation emitted is conveyed along the waveguide 8 through the optical coupling surface 8c.

Figure 8:
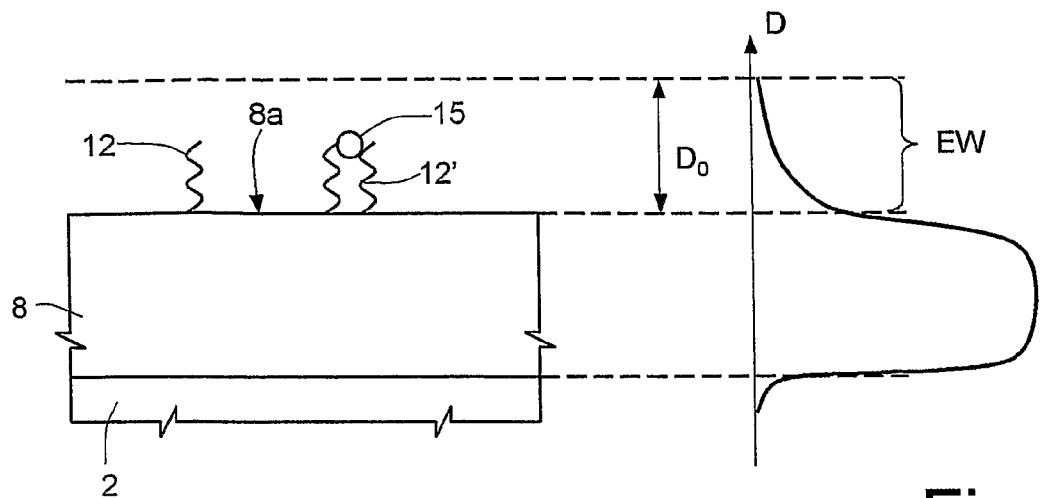
FIG. 8 shows a distribution of intensity associated to a light radiation propagating in the chip of FIG. 1.

As shown schematically in FIG. 8, a part of the energy associated to the light radiation remains confined within the waveguide 8. However, a fraction of energy depending upon the ratio between the primary refraction index $N_1$ and the secondary refraction index $N_2$ exits through the interface 8a and gives rise to an evanescent wave EW outside the waveguide 8. The intensity of the evanescent wave EW decays exponentially as the distance D from the first interface 8a increases and becomes substantially negligible within the attenuation distance $D_0$. The fluorofors 15 of the hybridized DNA probes 12' are in any case located at a distance from the first interface 8a that is much shorter than the attenuation distance $D_0$ (normally, less than 100 nm). The energy of the evanescent wave EW is hence sufficient to excite the fluorofors 15, which emit light that can be detected by the optical sensor 25, at the characteristic wavelength. The optical sensor 25 is not, however, able to detect the radiation due to the evanescent wave EW, because the detection distance $D_S$ (5-7 cm) is much greater than the attenuation distance (1-2 μm). In other words, the intensity of the evanescent wave EW is substantially zero at the detection distance $D_S$ from the first interface 8a, where the optical sensor 25 is located.

The digital images IMG detected by the optical sensor 25 are sent to the compensator module 28 of the control unit 21, which balances the brightness level to compensate for the attenuation of the light radiation (and of the evanescent wave EW) along the waveguide 8 as the distance from the optical coupling surface 8c increases (the most distant fluorofors 15 are excited to a lesser extent on account of attenuation and might not be recognized correctly). The compensator module 28 supplies compensated images $IMG_C$ to the image processing module 30, which is designed for detection of the hybridized DNA probes 12', containing fluorofors 15, and of their position in the array.

The chip and the inspection apparatus described substantially enable elimination of the disturbance due to the excitation radiation of the fluorofors during the optical detection of hybridized DNA probes. The excitation radiation is in fact almost entirely confined within the waveguide, and the evanescent wave that exits in the direction of the detection chamber to excite the fluorofors is attenuated at a very short distance from the waveguide itself and does not reach the optical sensor. Advantageously, the inspection apparatus requires just one waveguide, since the radiation emitted by the fluorofors is collected directly by the optical sensor. The integration of the waveguide within the chip represents a further advantage of the invention. On the one hand, in fact, the geometry of the waveguide can be optimized so that the evanescent wave will have exactly the desired intensity. On the other hand, the integrated waveguide can be optically coupled to the excitation light source in a simple and precise way, and the microfluidic device is suited to carrying out the step of detection in a completely automatic way.

Figure 10:
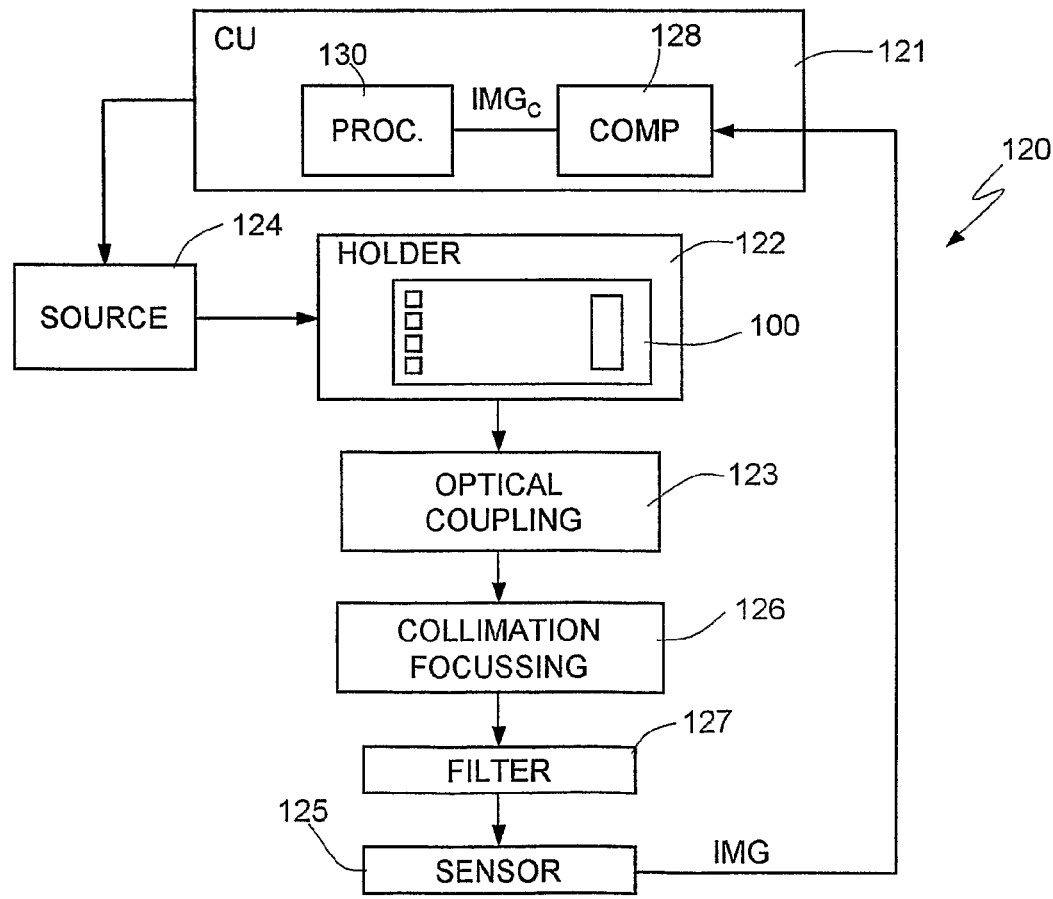
FIG. 10 is a simplified block diagram of an optical inspection apparatus for detection of nucleic acids which uses the chip of FIG. 9.
Figure 9:
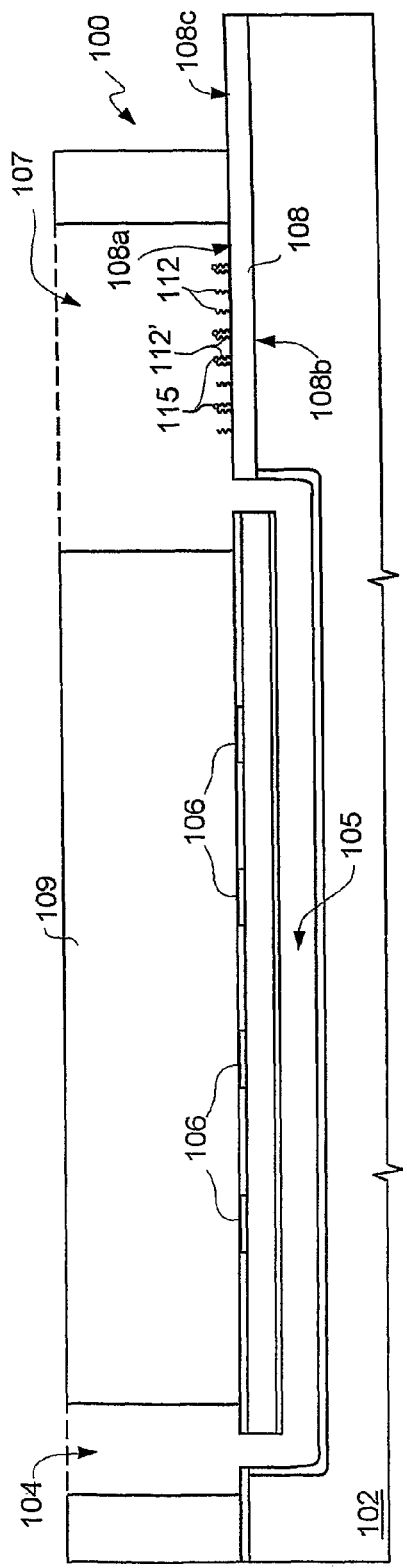
FIG. 9 is a cross-sectional view through a chip for nucleic acid analysis according to a second embodiment of the present invention.

FIGS. 9 and 10 show a different embodiment of the invention. In this case (FIG. 9), a chip 100 integrates a chemical microreactor that comprises a substrate 102 made of semiconductor material, inlet reservoirs 104, microfluidic channels 105 buried in the substrate 102, heaters 106, a detection chamber 107, and a waveguide 108.

The inlet reservoirs 104 and the detection chamber 107 are defined in a structural layer 109 arranged on the surface of the substrate 102 and are fluidly coupled to the microfluidic channels 105, as already explained with reference to FIGS. 1 and 2. As may be seen in FIG. 9, the substrate 102 projects beyond the structural layer 109 on the side of the detection chamber 107.

The detection chamber 107 is formed above the waveguide 108 and accommodates a plurality of DNA probes 112, arranged in predetermined positions so as to form an array. The DNA probes 112 are moreover grafted to the waveguide 108, which forms the bottom of the detection chamber 107. Hybridized DNA probes 112' contain fluorofors 115.

The waveguide 108 comprises a plane layer of optically conductive material having a predetermined primary refraction index $N_1$, for example appropriately doped silicon oxynitride or silicon oxide. Furthermore, the waveguide 108 is formed on the substrate 102 and extends at the bottom of the array of DNA probes 12 and also outside the detection chamber 7, for example in a direction opposite to the microfluidic channels 105. A portion of the waveguide 108 laterally external to the structural layer 109 defines an optical coupling surface 108c. Preferably, the optical coupling surface 108c is free and arranged directly facing outwards.

Illustrated in FIG. 10 is an inspection apparatus 120 of an optical type, which comprises a control unit 121, a holder 122 for housing an example of the chip 100, a light source 124, an optical coupling element 123, and an optical sensor 125, which is provided with a collimation and focusing device 126 and an interferential filter 127, having a passband centred around the wavelength of emission characteristic of the fluorofors 115.

Furthermore, the control unit 121 comprises a compensator module 128, which receives digital images IMG from the optical sensor 125, and an image processing module 130.

Figure 11:
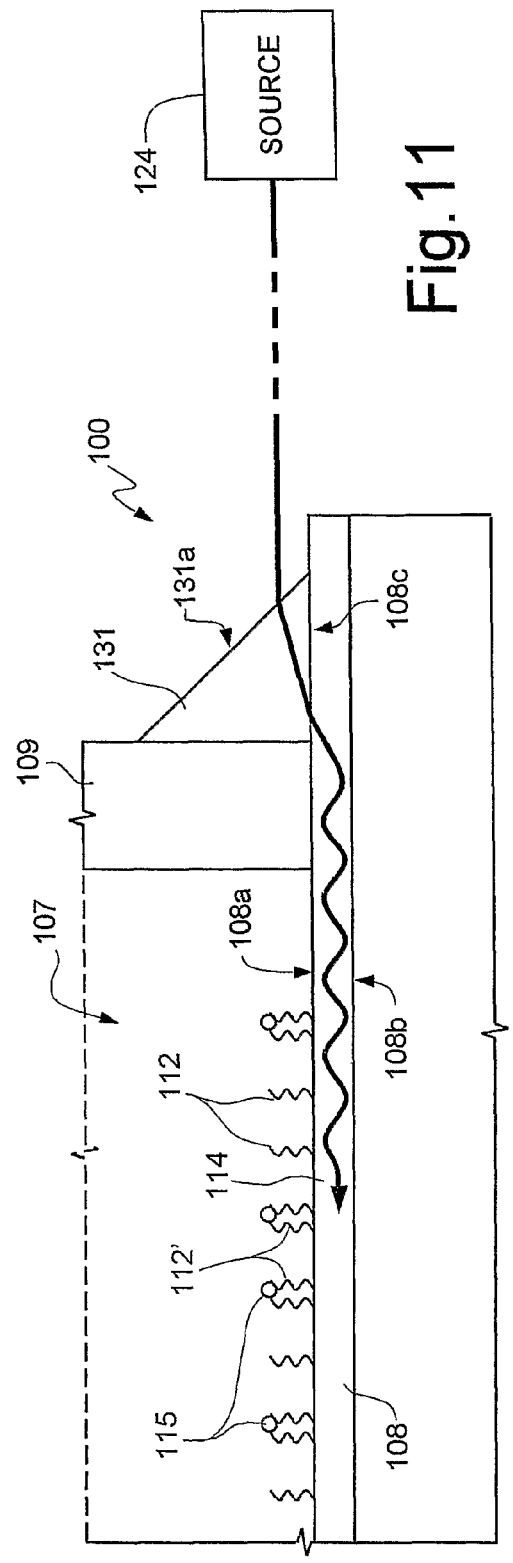
FIG. 11 is a schematic illustration of a detail of the chip of FIG. 9 loaded into the apparatus of FIG. 10.

As shown in FIG. 11, the optical coupling element 123 comprises an optical prism 131 having an input surface 131a, which receives the radiation emitted by the light source 124, and an output surface, which faces the optical coupling surface 108a of the chip 100 when it is loaded into the holder 122. The optical prism 131 is configured so as to convey within the waveguide 108 the radiation coming from the light source 124.

Finally, it is evident that modifications and variations may be made to the chip and to the apparatus described herein, without departing from the scope of the present invention, as defined in the annexed claims. For example, the waveguide can be made of any material and using any technique, in particular those suited to being integrated in the processes of fabrication of semiconductor devices. The hybridized DNA probes may be in liquid suspension, instead of immobilized at the bottom of the detection chamber. In this case, only the fluorofors included in DNA probes that are located in the immediate neighbourhood of the waveguide, within the attenuation distance, are excited. The optical prism for coupling to the light source, when present, can be integrated in the chip (for example bonded), instead of forming part of the detection apparatus. Finally, the chip may also comprise just the detection chamber, in addition to the waveguide.

The invention claimed is:

1. A chip for nucleic acid analysis, comprising:
   a substrate made of semiconductor material;
   a detection chamber for accommodating nucleic acid probes;
   a plurality of microfluidic channels buried in said substrate and fluidly coupled to said detection chamber;
   a plurality of heaters connectable to external electric power sources for controllably releasing thermal power to said microfluidic channels; and
   a waveguide formed on said substrate and set adjacent to said detection chamber, wherein said detection chamber is defined in a structural layer above said waveguide, so that an evanescent wave will extend from an interface of said waveguide into said detection chamber when an excitation radiation is conveyed within said waveguide.

2. The chip according to claim 1, wherein said waveguide is a plane waveguide.

3. The chip according to claim 2, wherein said waveguide comprises a plane layer made of a material selected from the group consisting of: silicon oxide and silicon oxynitride.

4. The chip according to claim 3, wherein said waveguide contains a dopant species with a predetermined concentration, said dopant species being selected from the group consisting of: phosphorus, germanium, boron, and titanium.

5. The chip according to claim 1, wherein said waveguide comprises an optical coupling surface optically accessible from outside.

6. The chip according to claim 5, wherein said optical coupling surface forms a predetermined angle with respect to said interface so that radiation incident from outside on said optical coupling surface is conveyed within said waveguide.

7. The chip according to claim 5, wherein said waveguide and said waveguide extends laterally outside said structural layer so that a portion of said waveguide laterally external to the structural layer defines said optical coupling surface.

8. The chip according to claim 1, wherein said nucleic acid probes are grafted to said waveguide.

9. The chip according to claim 8, wherein said waveguide comprises a core and a cladding coating opposite faces of said core, said cladding being thinned out where said nucleic acid probes are grafted.

10. An optical apparatus for the inspection of nucleic acid probes, comprising:
 a holder for housing a chip for nucleic acid analysis, containing nucleic acid probes;
 a light source for supplying an excitation radiation to said nucleic acid probes;
 an optical sensor arranged so as to receive radiation coming from said nucleic acid probes; and
 a chip for nucleic acid analysis according to claim 5 loaded into said holder.

11. The apparatus according to claim 10, wherein said waveguide is coupled to said light source through said optical coupling surface.

12. The apparatus according to claim 11, wherein said light source is arranged so as to convey the excitation radiation directly towards said optical coupling surface.

13. The apparatus according to claim 11, comprising an optical coupling element arranged between said light source and said optical coupling surface.

14. The apparatus according to claim 13, wherein said optical coupling element comprises an optical prism having an input surface for receiving the excitation radiation from said light source and an output surface facing said optical coupling surface.

15. The apparatus according to claim 10, comprising a control unit for receiving digital images from said optical sensor.

16. The apparatus according to claim 15, wherein the control unit comprises a compensator module for balancing a level of brightness in said digital images to compensate for the attenuation of the excitation radiation and of said evanescent wave along said waveguide as a distance from said optical coupling surface increases.

* * * * *